United States Patent
Lv et al.

(10) Patent No.: US 11,066,500 B2
(45) Date of Patent: Jul. 20, 2021

(54) CROSSLINKABLE SURFACTANTS

(71) Applicant: Dow Global Technologies LLC, Midland, MI (US)

(72) Inventors: Bo Lv, Shanghai (CN); Cheng Shen, Shanghai (CN); Shaoguang Feng, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 279 days.

(21) Appl. No.: 16/320,239

(22) PCT Filed: Jul. 27, 2016

(86) PCT No.: PCT/CN2016/091841
§ 371 (c)(1),
(2) Date: Jan. 24, 2019

(87) PCT Pub. No.: WO2018/018444
PCT Pub. Date: Feb. 1, 2018

(65) Prior Publication Data
US 2019/0276574 A1    Sep. 12, 2019

(51) Int. Cl.
*C08F 212/08* (2006.01)
*C08F 220/18* (2006.01)
(Continued)

(52) U.S. Cl.
CPC ............ *C08F 212/08* (2013.01); *C07C 2/76* (2013.01); *C08F 2/30* (2013.01); *C08F 220/18* (2013.01);
(Continued)

(58) Field of Classification Search
CPC .......... C08F 212/08; C08J 3/07; C11C 3/003; C11C 3/02; C11C 3/06
See application file for complete search history.

(56) References Cited

U.S. PATENT DOCUMENTS 4,408,084 A * 10/1983 Langdon .................. C08G 4/00
568/593
6,001,913 A * 12/1999 Thames .................. C08K 5/098
524/21
(Continued)

FOREIGN PATENT DOCUMENTS

| CN | 103450409 | 12/2013 |
|----|-----------|---------|
| CN | 103864725 | 6/2014  |

OTHER PUBLICATIONS

International Search Report & Written Opinion for related PCT Application PCT/CN2016/091841, dated Apr. 28, 2017 (13 pgs).
(Continued)

*Primary Examiner* — Mark S Kaucher
(74) *Attorney, Agent, or Firm* — Brooks, Cameron & Huebsch, PLLC

(57) ABSTRACT

A crosslinkable surfactant useful for preparing an emulsion polymerization composition; the crosslinkable surfactant including (a) a crosslinkable functionality and a hydrophobic tail with a Tung oil derivative structure, and (b) a polyalkylene oxide or polyglycerin part as hydrophilic head; an emulsion polymerization process using the crosslinkable surfactant; an emulsion polymerization composition; and a process for preparing the emulsion polymerization composition.

16 Claims, 7 Drawing Sheets

(51) Int. Cl.
  *C08J 3/07* (2006.01)
  *C08J 3/24* (2006.01)
  *C11C 3/06* (2006.01)
  *C07C 2/76* (2006.01)
  *C11C 3/00* (2006.01)
  *C08F 2/30* (2006.01)
  *C08F 2/26* (2006.01)
  *C08F 220/28* (2006.01)

(52) U.S. Cl.
  CPC . *C08J 3/07* (2013.01); *C08J 3/24* (2013.01); *C11C 3/006* (2013.01); *C11C 3/06* (2013.01); *C08F 2/26* (2013.01); *C08F 220/1804* (2020.02); *C08F 220/281* (2020.02); *C08F 2810/20* (2013.01)

(56) References Cited

U.S. PATENT DOCUMENTS

| | | | |
|---|---|---|---|
| 6,071,859 A * | 6/2000 | Ogawa | A01N 37/12 504/151 |
| 6,924,333 B2 | 8/2005 | Bloom et al. | |
| 7,754,823 B2 | 7/2010 | Binder et al. | |
| 2003/0187103 A1* | 10/2003 | Bloom | C09D 5/027 524/35 |
| 2005/0119501 A1* | 6/2005 | Tammer | C08F 4/34 562/4 |
| 2011/0065856 A1 | 3/2011 | Anchor | |
| 2015/0232590 A1* | 8/2015 | Tartarin | C08K 5/14 526/200 |
| 2017/0218107 A1* | 8/2017 | Littich | C08F 220/68 |
| 2017/0247368 A1* | 8/2017 | Mickle | A61K 39/39 |

OTHER PUBLICATIONS

International Preliminary Report for Patentability for related PCT Application PCT/CN2016/091841, dated Feb. 7, 2019 pgs).

* cited by examiner

CROSSLINKABLE SURFACTANTS

This application is a National Stage Application under 35 U.S.C. § 371 of International Application Number PCT/CN2016/091841, filed Jul. 27, 2016 and published as WO 2018/018444 on Feb. 1, 2018, the present application claiming priority thereto and the entire contents of which are incorporated herein by reference in its entirety.

FIELD

The present invention is related to a crosslinkable surfactant, a composition or a formulation containing the crosslinkable surfactant, and the use of the crosslinkable surfactant in emulsion polymerization and other applications.

BACKGROUND

Emulsion polymerization of monomers such as acrylic, vinylic, or styrenic monomers is known in the art. In carrying out the emulsion polymerization, a surfactant is typically added to the polymerization recipe. The surfactant is used to emulsify monomers during the polymerization; and to control both the particle size of the resulting polymer particles and the stability (e.g., storage stability and freeze/thaw stability) of the emulsion for preventing precipitation. In known film applications, it is known that small molecules of the known surfactants, with time, migrate towards the surface of a film after the film is formed with binder polymers. Once the migrated surfactant reposes on the surface of a coating layer, the surfactant molecules are susceptible to being rinsed off from the surface of the coating layer when water is applied to the surface of the coating.

Organic conventional surfactant molecules can change the film's surface properties or can form hydrophilic domains within the film upon phase separation; the above migration phenomenon can lead to a series of problems in the performance of the film. Film properties such as adhesion, hardness, dirty pick up resistance (DPUR), water resistance, and water whitening resistance can be affected by surfactant molecules on the film's surface. For example, once water penetrates between a dried emulsion film and a substrate after immersing in water, water whitening occurs because the surfactant and salts, which are trapped in the interstices between particles, swell with water to a larger size. Then the surfactant and salts are large enough and exhibit a refractive index different from the polymer, such that the surfactant and salts scatter light to provide a whitening effect. In addition, water whitening can also be an expression of water resistance. Accordingly, a less whitening effect (and therefore a greater water resistance) can be exhibited by the film when the adhesion between the film layer and substrate is strong enough to prevent water penetration between a film coating layer and the surface of a substrate.

In an attempt to minimize the migration of the surfactant molecules which are used in emulsion polymerization, heretofore, conventional surfactants have been replaced with crosslinkable surfactants (also referred to as "reactive surfactants") in an emulsion polymerization recipe. However, during the emulsion polymerization preparation, some of the known reactive surfactants or crosslinkable surfactants may not completely polymerize into the polymer chain; and therefore, non-polymerized surfactants remain in the emulsion; and similar to conventional surfactants, with time, such non-polymerized surfactants remaining in the polymer can migrate to the surface of a coating layer made using the emulsion polymerization composition.

For example, SR-10 is a known reactive surfactant, commercially available from Adeka Company. Allyl groups are present as the reactive functionality in SR-10. However, one disadvantage of SR-10 is the lack of reactivity of the allyl groups in SR-10; and thus SR-10 has a poor bonding ability during a chasing process as SR-10 can only partially react in an emulsion polymerization process (for example, the allyl groups in SR-10 are less than 60% reactive in a styrene-acrylate emulsion polymerization process).

Further crosslinking by the allyl groups in SR-10 with unreacted free surfactants does not occur, therefore, the problems encountered using SR-10 are the same as described above using conventional surfactants.

SUMMARY

The present invention is directed to developing a technical solution to the migration problem of known surfactants when used in an emulsion polymerization composition. In accordance with the present invention, a particular crosslinkable functional group or groups is introduced into a surfactant molecule to form a crosslinkable surfactant. The crosslinkable surfactant can then be used in a monomer emulsion composition. The monomer emulsion composition can be subjected to an emulsion polymerization process to prepare a film or coating. The functional group(s) incorporated into the crosslinkable surfactant can react with a polymer backbone; or the functional group(s) incorporated into the crosslinkable surfactant can react with themselves; not only during a chasing process, but also during a film forming process at application conditions. As a result of either of the above two reactions, the migration effect of the surfactant molecules can be eliminated or at least minimized to a level such that the performance of the polymer with the crosslinkable surfactant incorporated therein is improved.

One embodiment of the present invention is directed to a crosslinkable surfactant. The crosslinkable surfactant includes the reaction product of (a) Tung oil acid and (b) at least one alkylene oxide. The above reaction product results in a modified Tung oil acid (or also referred to herein as a Tung oil derivative) with the crosslinkable characteristic. For example, Tung oil acid may be modified with a hydrophilic functionality or functionalities; and the modified Tung oil acid molecules may then be added to a monomer emulsion formulation as a novel crosslinkable surfactant, which in turn is useful for preparing a film or coating by emulsion polymerization.

The structure of Tung oil acid, component (a), has some advantages including for example the following beneficial features:

(1) The C—C bonds in the structure of Tung oil acid can polymerize during a radical polymerization process. This polymerization of C—C bonds feature of the Tung oil acid structure indicates that Tung oil derivatives includes the basic requirement of having reactive functionalities in reactive surfactants; and (2) The conjugated C—C bonds in the structure of Tung oil acid can be oxidized under air and form a highly crosslinked structure. This oxidation of conjugated C=C bonds feature of the structure of Tung oil acid indicates that even if the Tung oil derivative molecules cannot fully crosslink during a polymerization process, when the molecules are placed under air, the molecules can further react with themselves to further reduce the amount of free surfactant in a system.

Another embodiment of the present invention is directed to a monomer emulsion composition or formulation (or also referred to as a pre-emulsion or precursor emulsion solution) including (a) the modified Tung oil acid crosslinkable surfactant described above; (b) a monomer selected from various monomers such as styrene, butyl acrylate, and the like; and (c) water.

Still another embodiment of the present invention is directed to an emulsion polymerization composition or formulation (or also referred to as a polymerizable emulsion solution) including (a) the monomer emulsion formulation described above; and (b) an activator.

Yet another embodiment of the present invention is directed to a polymerization reaction product such as a film or coating made from the emulsion polymerization formulation described above.

Other embodiments of the present invention include a process for preparing the crosslinkable surfactant described above; a process for preparing the monomer emulsion formulation described above; a process for preparing the emulsion polymerization formulation described above; and a process for preparing the polymerization reaction product; and a process for using the polymerization reaction product to produce, for example, a film or coating.

BRIEF DESCRIPTION OF THE DRAWINGS

For the purpose of illustrating the present invention, the drawings show a form of the present invention which is presently preferred. Therefore, the following drawings illustrate non-limiting embodiments of the present invention wherein.

DETAILED DESCRIPTION

Figure 1:
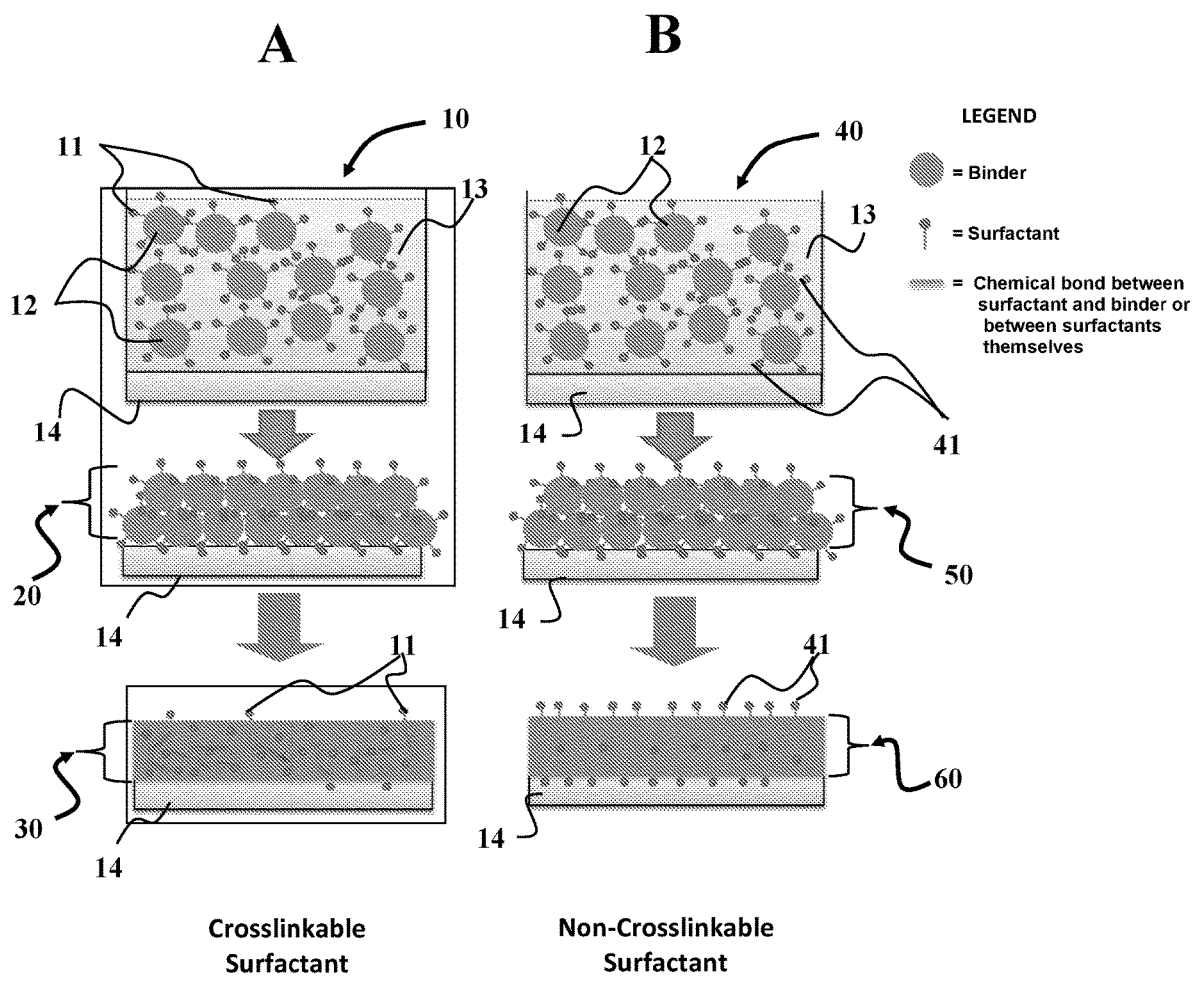
FIG. 1 is a schematic flow diagram showing the occurrence of surfactant migration when using a crosslinkable surfactant (Process A) versus the occurrence of surfactant migration when using a known surfactant (Process B).

Tung oil and derivatives of Tung oil, such as Tung oil acid, are natural products which are capable of exhibiting self-crosslinking abilities. For example, normally, the self-crosslinking action of Tung oil in the presence of oxygen takes about 3 to about 7 days when exposed under atmosphere and at room temperature. The curing process of a formulation containing Tung oil can be accelerated or decelerated with catalysts; and therefore, the curing of Tung oil can be controlled in some applications. For example, because of Tung oil's self-crosslinking ability, Tung oil finds use in applications such as wood finishing, water-paper umbrella producing, printed circuit board manufacturing, and other enduse applications.

The present invention is directed to a crosslinkable surfactant wherein the crosslinkable surfactant comprises a modified Tung oil acid (also referred to herein as a Tung oil derivative). The modified Tung oil acid includes the reaction product of (a) Tung oil acid and (b) at least one alkylene oxide to form the crosslinkable surfactant of the present invention. An objective of the present invention is to produce a crosslinkable surfactant such that when the surfactant is used in an emulsion polymerization process to produce, for example a film, the surfactant does not migrate towards the surface of the film formed from said emulsion polymerization formulation; or at least such that the migration of the surfactant to the surface of the film is minimized. Such crosslinkable surfactant would be beneficial to the emulsion polymerization industry.

The chemical structure of Tung oil acid is shown in the following chemical formula designated as Structure (I):

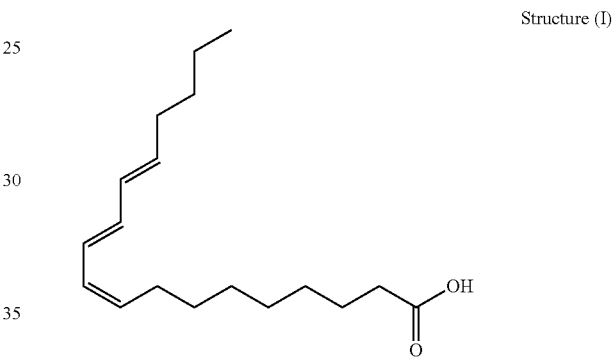

Structure (I)

In Structure (I), a conjugated cis carbon-carbon double bound is located at the
9-position and trans carbon-carbon double bounds are located at the 11-position and the 13-position.

When the above Tung oil acid is modified in accordance with the present invention an effective crosslinkable surfactant can be produced that is useful in emulsion polymerization. In one embodiment, for example, the crosslinkable surfactant of the present invention can include a surfactant having the following generic chemical formula designated as Structure (II):

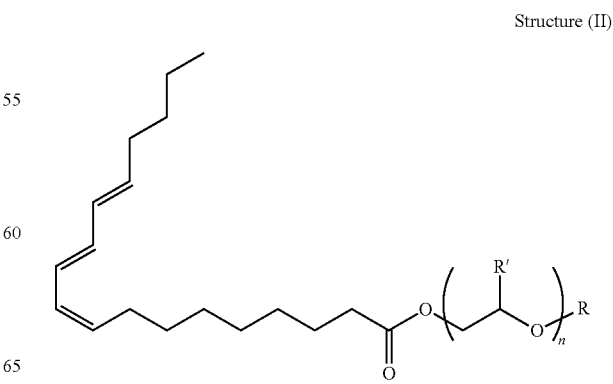

Structure (II)

wherein R can be hydrogen, $SO_3^-$, or $PO_3^-$; R' can be hydrogen or an alkyl group having from C1 to about C6 carbon atoms; and n can be an integer from 0 to about 50.

In another embodiment, the crosslinkable surfactant of the present invention can include, for example, the following generic chemical formula designated as Structure (III):

Structure (III)

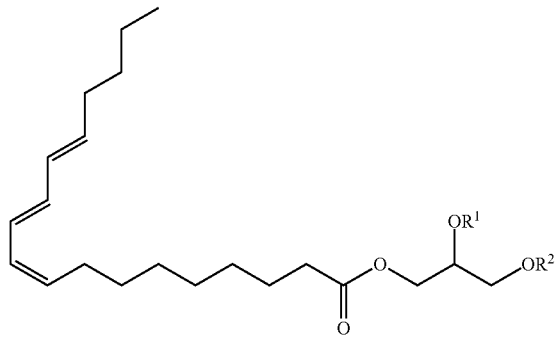

wherein $R^1$ and $R^2$, each individually and separately, can be an alkyl having from C1 to about C10 carbon atoms, an aryl having from C5 to about C10 carbon atoms, a polyol, a polyol ester, hydrogen, $SO_3^-$, or $PO_3^-$; and $R^1$ and $R^2$ can be the same or different.

As aforementioned, the Tung oil derivative includes the reaction product of (a) Tung oil acid and (b) at least one alkylene oxide to form the crosslinkable surfactant of the present invention. General examples of the alkylene compounds useful for making the crosslinkable surfactant of the present invention include one or more alkylene oxide compounds selected from the group consisting of ethylene oxide, propylene oxide, butylene oxide, and mixtures thereof. In one preferred embodiment, the crosslinkable surfactant of the present invention includes ethylene oxide.

In one embodiment, the crosslinkable surfactant product of the present invention may include for example an ethoxylated Tung oil acid such as Tung oil acid-7 (TOA-7) which is a nonionic surfactant; Tung oil acid-10 (TOA-10) which is a nonionic surfactant; a sulfate salt of ethoxylated Tung oil acid-7 (STOA-7); a sulfate salt of ethoxylated Tung oil acid-10 (STOA-10); and mixtures thereof.

The average molecular weight of the crosslinkable surfactant product may depend on the number of alkylene oxide units. Typically, the average molecular weight of the crosslinkable surfactant can be from about 500 to about 3,000 in one general embodiment.

One embodiment of the present invention includes modifying the structure of Tung oil with a series of hydrophilic chains such that the modified Tung oil is useful as a crosslinkable surfactant. The amphiphilic Tung oil derivatives of the present invention, as crosslinkable surfactants, are easy to prepare and have low surface tension, low critical micelle concentration (CMC), good $Ca^{2+}$ stability and emulsion particle size controlling abilities. When compared to a control surfactant prepared from saturated C18 fatty acid, it is found that a Tung oil derivative surfactant can significantly improve water whitening resistance in styrene-acrylate emulsion polymerization system which indicates the crosslinking ability of the surfactant and which supports the hypothesis herein that these functional groups can react not only during the polymerization but also during the film formation process. As described in the Examples herein, the novel modified Tung oil of the present invention can remain stable for greater than (>) 1.5 month at 50° C. which shows that the novel modified Tung oil of the present invention and its derivatives can provide good in-can stability.

Generally, in one embodiment, the process of preparing the crosslinkable surfactant of the present invention includes, for example, the steps of: (a) alkoxylating Tung oil acid; (b) sulfating the alkoxylated compound from step (a) to form a reaction product; and (c) neutralizing and diluting the reaction product from step (b) with a medium such as water.

For example, Tung oil acid can be alkoxylated by reacting the Tung oil acid with an alkylene oxide compound in the presence of an alkaline catalyst. The various alkylene oxide compounds useful in the present invention may include for example EO, PO and BO, and mixtures thereof. The alkaline catalyst useful in the present invention may include for example KOH. This alkoxylation step (a) is used to produce for example the crosslinkable surfactant referred to as "TOA-7" and "TOA-10".

For example, a TOA alkoxylate can be sulfated via a sulfamic acid ($NH_2SO_3H$) process by treating the TOA alkoxylate with the sulfamic acid compound and optionally in the presence of an activator such as urea. This sulfating step is used to produce for example STOA-7 and STOA-10. Another process to prepare a sulfate compound useful in the present invention may include for example $SO_3$ process, followed with a base neutralization step. The various bases useful in this $SO_3$ process may include for example KOH, NaOH, ammonia, and mixtures thereof.

The reaction product of step (b) can be diluted with a medium such as water, solvent or a mixture thereof to provide a crosslinkable surfactant product of the present invention. Then, the crosslinkable surfactant product may subsequently be used to form a monomer emulsion formulation. When the dilution medium is a water component, the water useful in the present invention may include for example deionized water, tap water, distilled water, and mixtures thereof. The various solvent compounds useful in the present invention may include for example an alcohol such as ethanol, isopropanol, and the like; and mixtures thereof.

In addition to other beneficial properties that the surfactant exhibits, one of the more beneficial properties is the surfactant's stability, which can be expressed by $Ca^{2+}$ stability. In one general embodiment, the stability of the surfactant can be for example from about 30% to about 50%, and from about 35% to about 45% in another embodiment.

The process of emulsion polymerization is a free radical polymerization that usually starts with a monomer emulsion formulation. Accordingly, one broad embodiment of the present invention includes a monomer emulsion formulation including: (a) the crosslinkable surfactant described above; (b) at least one monomer, and (c) water.

Generally, the monomer emulsion formulation, before the monomer emulsion is subjected to polymerization, includes a mixture of (a) the crosslinkable surfactant described above; (b) at least one monomer, and (c) water. The monomer emulsion formulation may be prepared by first dissolving the crosslinkable surfactant in water. The interior of the micelle formed in the emulsion provides the site necessary for polymerization.

In preparing the monomer emulsion formulation of the present invention, a first required component (a) is the crosslinkable surfactant described above; and in one embodiment, the crosslinkable surfactant may be the surfactants illustrated in Structures (II) and (Ill) above. Examples of the crosslinkable surfactant include, in one embodiment, a surfated Tung oil acid ethoxylate.

In general, the amount of the crosslinkable surfactant in the monomer emulsion formulation can be in the range of from about 0.01 wt % to about 20.0 wt % in one embodiment, from about 0.1 wt % to about 10.0 wt % in another embodiment, and from about 0.2 wt % to about 5.0 wt % in still another embodiment, based on the components in the monomer emulsion formulation.

In preparing the monomer emulsion formulation of the present invention, a required component (b) includes at least one monomer compound. In general, component (b), the monomer compound may include one or more of styrene monomers such as styrene; acrylate monomers such as acrylic acid, butyl acrylate, and acrylamide; and mixtures thereof. In one embodiment, the crosslinkable surfactant can be added to a formulation, such as styrene butyl acrylate (St-BA) formulation.

The monomer emulsion formulation of the present invention includes a medium, component (c) such as water, a solvent or a mixture thereof. When the medium useful for preparing the monomer emulsion formulation of the present invention is a water component, the water useful in the present invention may include for example deionized water, tap water, distilled water, and mixtures thereof. The various solvent compounds useful in the present invention may include for example an alcohol such as ethanol, isopropanol, and the like; and mixtures thereof.

In addition to the crosslinkable surfactant and the monomer compound, the monomer emulsion formulation of the present invention other optional additives. The other optional additives may include for example nonionic surfactants, anionic surfactants, wetting agents, dispersants, and mixtures thereof. The crosslinkable surfactant and/or the monomer compound of the monomer emulsion formulation can also be mixed with other ingredients prior to making up the final monomer emulsion formulation including for example, nonionic surfactants, dispersants, and mixtures thereof.

In a broad embodiment, the process of preparing the monomer emulsion formulation of the present invention includes admixing: (a) the crosslinkable surfactant described above; (b) at least one monomer, and (c) water under process conditions to form the monomer emulsion formulation.

The process and type of equipment used to prepare the monomer emulsion formulation of the present invention includes blending or mixing the above components in mixing equipment or vessels known in the art. For example, the preparation of the monomer emulsion formulation of the present invention is achieved by blending in known mixing equipment. The preparation of the monomer emulsion formulation of the present invention, and/or any of the steps thereof, may be a batch process in one embodiment.

In one preferred embodiment, the process of preparing the monomer emulsion formulation of the present invention includes, for example, (a): preparing a water solution of reactive surfactant; (b) adding one or more monomers into the water solution; and (c) stirring the resultant mixture from step (b) until the viscosity of the mixture appears to increase as determined by visual inspection.

Another broad embodiment of the present invention includes an emulsion polymerization formulation or composition (or also referred to herein as a polymerizable emulsion solution or polymer emulsion). Generally, the emulsion polymerization composition, before the emulsion polymerization composition is subjected to polymerization, includes a mixture of (a) the monomer emulsion formulation described above; and (b) at least one compound, referred to as an activator or an initiator, which functions to activate the polymerization reaction.

In preparing the polymer emulsion composition of the present invention, the first required component (a) is the monomer emulsion formulation described above. In general, the amount of monomer emulsion formulation, component (a), in the polymer emulsion composition can be in the range of from about 30 wt % to about 70 wt % in one embodiment, from about 40 wt % to about 60 wt % in another embodiment, and from about 45 wt % to about 50 wt % in still another embodiment, based on the components in the polymer emulsion composition.

In preparing the polymer emulsion composition of the present invention, the required component (b) includes at least one initiator compound. In general, component (b), the initiator compound may include for example one or more of potassium persulfate, ammonium persulfate, benzoyl peroxide; and mixtures thereof.

The concentration of the initiator compound, component (b), included in the emulsion polymerization composition of the present invention may range generally from about 0.01 wt % to about 5.0 wt % in one embodiment, from about 0.05 wt % to about 2.0 wt % in another embodiment, and from about 0.1 wt % to about 1.0 wt % in still another embodiment, based on the components in the polymer emulsion composition.

The polymer emulsion composition may include other optional additives. For example, the optional additives useful in the polymer emulsion composition may include nonionic surfactants, anionic surfactants, wetting agents, dispersants, and mixtures thereof.

In a broad embodiment, the polymer emulsion can be prepared by admixing (a) the monomer emulsion formulation described above; and (b) at least one initiator described above; and then subjecting the above mixture under process conditions, such as by heating the mixture, to form a polymer emulsion. Mixing and heating the above mixture to form a polymer emulsion is generally carried out in a continuous and simultaneous manner in a vessel. The process and type of equipment used to prepare the polymer emulsion includes mixing and heating equipment and vessels known in the art. For example, the preparation of the polymer emulsion composition of the present invention is achieved by blending and heating, in known mixing equipment, the monomer emulsion formulation and the at least one initiator and heating the mixture in the same vessel.

In one embodiment, the process for preparing the polymer emulsion of the present invention includes (a) preparing the monomer emulsion by pr-emulsifying a first part of the surfactant composition (component a) with sodium bicarbonate, water and the above mentioned monomers in a flask while stirring the mixture at room temperature (about 25° C.) for about 30 minutes (min); (b) adding a second part of the surfactant composition (component a) and water into a reactor vessel; (c) heating the reactor contents to a temperature in the range of from about 80° C. to about 90° C.; (d) adding a first part of ammonium persulfate into the reactor, (e) adding in a dropwise manner the pre-emulsion with a second part of ammonium persulfate during a period of about 3 hours (hr); (f) after the addition in step (e), maintaining the reaction mixture at the same temperature for 1 hour such that an emulsion polymerization is performed to form a polymer emulsion; (g) cooling the polymer emulsion to about 65° C., (h) once the polymer emulsion is cooled down to 65° C., adding an additional amount of re-dox initiator to the polymer emulsion to further consume any residual monomers and allowing the polymer emulsion to react at 65° C. for a period of 30 min; (i) cooling the polymer emulsion to about 40° C.; (j) once the polymer emulsion is cooled down to 40° C., adjusting the pH of the polymer emulsion with aqueous ammonia; and (k) filtering the polymer emulsion to obtain the polymer emulsion product, i.e., the polymer emulsion composition that can be polymerized, but which is prepared prior to subjecting the polymer emulsion composition to a reaction process to form a film or coating product.

The polymer emulsion composition that is prepared by the above process of the present invention exhibits several unexpected and unique properties; and some properties of the polymer emulsion are due to the use of the crosslinkable surfactant described above which imparts beneficial properties to the polymer emulsion. For example, important properties of the polymer emulsion composition can include improved polymerization stability, mechanical stability, and water resistance.

Generally, the polymer emulsion composition may contain polymerization residue, which is understood to being aggregated polymers. The polymerization residue of the polymer emulsion prepared with the crosslinkable surfactant of the present invention can be lower than 2,000 ppm in one embodiment, lower than 1,200 ppm in another embodiment, and lower than 600 ppm in still another embodiment. The polymer emulsion stability may be measured by the procedure described herein under the Emulsion Test Methods of the Examples.

Another property that the polymer emulsion composition exhibits is formulation stability. The formulation stability may be expressed by $Ca^{2+}$ stability. $Ca^{2+}$ stability is measured by adding calcium chloride ($CaCl_2$) aqueous solution into the polymer emulsion, and then checking the appearance of the resultant mixture. The % $CaCl_2$ (10% wt. aq. soln.) in the polymer emulsion may be higher than 5 wt % in one embodiment, higher than 10 wt % in another embodiment, and higher than 14 wt % in still another embodiment. The $Ca^{2+}$ stability can be determined using the procedure described herein under the Emulsion Test Methods of the Examples.

In a broad embodiment, a process for preparing a polymeric product or article includes first preparing a polymer emulsion, and then coating a substrate with the polymer emulsion, i.e., subjecting a substrate to a polymer emulsion composition. For example, in one embodiment, the reaction process may include (a) applying the polymer emulsion composition to a substrate; and (b) allowing the polymer emulsion to form a polymeric product such as a film or coating, for example by evaporization at room temperature. The applying step (a) can be carried out by any known means such as rolling, brushing, spraying, and the like. The step (b) can be carried out at a temperature of from about 0° C. to about 100° C. in one embodiment.

Because of the beneficial properties exhibited by the polymer emulsion composition such as for example improved stability, improved water resistance, and decreased migration, the polymer emulsion composition of the present invention is advantageously used in various applications including for example architectural coatings and adhesives.

In one embodiment of the present invention, a polymer emulsion composition containing the crosslinkable surfactant can be used in a coating application.

For example, in FIG. 1 there is shown a generic schematic illustration of two processes: a process labeled "Path A" and a process labeled "Path B" which are schematic representations to show surfactant migration after drying coating film layers as shown in FIG. 1.

In the process of the present invention (Path A), a polymer emulsion generally indicated by numeral 10 in FIG. 1 includes a surfactant 11 on a binder 12 in liquid medium 13. In FIG. 1, the polymer emulsion 10 is shown applied wet to a substrate 14. After drying the liquid medium from the polymer emulsion a coating film, generally indicated by numeral 20, forms which includes the surfactant 11 and binder 12 or in another embodiment the surfactant 11 itself. Upon polymerizing the coating film 20, the crosslinkable surfactants react with the binder and the surfactant 11 is bonded to the binder polymer backbone and a uniform coating layer, generally indicated by numeral 30, is formed with the surfactant 11 embedded in the coating layer 30. Because the surfactant reacts with a polymer backbone, the migration of the surfactants to the surface of coating film layers is significantly reduced. The crosslinkable surfactants react with the polymer backbone in various processes such as a chasing process and/or a film forming process. The use of the crosslinkable surfactants of the present invention lead to a decrease in migration or to no migration.

With reference to FIG. 1 again, there is shown an approach indicated as Path B (Comparative Example). In Path B, the polymer emulsion, generally indicated by numeral 40, includes a non-crosslinkable surfactant 41 on a binder 12 in liquid medium 13. After evaporating away or drying the liquid medium, a coating generally indicated by numeral 50 is formed. Upon polymerizing the coating 50, the non-crosslinkable surfactant 41 does not react with the binder 12; and thus, the non-crosslinkable surfactant 41 can be free to migrate to the interface between the substrate 14 and the coating, generally indicated by numeral 60, and/or to the surface of the coating 60. The surfactant in the interface can induce a decrease in the adhesion of the coating to the substrate. Other properties that may be detrimentally affected by the use of non-crosslinkable surfactants may include a reduction in one or more of the following properties: hardness, DPUR, water resistance and water whitening resistance among other properties.

On the other hand, the film of the present invention made by the emulsion polymer composition of the present invention exhibits several performance properties. For example, the use of the crosslinkable surfactants of the present invention can lead to low/no migration of molecules of the surfactant to the surface of a film when the crosslinkable surfactant is used in the emulsion polymer composition. And, because the surfactant does not migrate to the interfaces of the composition, the adhesion of the film to a substrate is increased, in addition to the increase in hardness, DPUR, water resistance and water whitening resistance properties of the film.

Water resistance is a beneficial property of the emulsion film made from emulsion polymer composition of the present invention. The water resistance property of the film is determined by measurement of water whitening; and the color measurement system is expressed by Lab color model known in the art. "L" means luminosity ranging from 0 to 100; in the scale of luminosity "L", a value of "0" means black and a value of "100" means white. The "L" value for the film of the present invention may be in the range of from about 25 to about 100 in one embodiment, from about 25 to about 80 in another embodiment, and from about 25 to about 60 in still another embodiment. The water resistance property of the film can be determined using the procedure described herein under the Emulsion Test Methods of the Examples.

Water whitening resistance of a coating or film described above is generally lower when crosslinkable surfactants are used. By visual inspection, less whitening of a film can be observed when the crosslinkable surfactant is use compared with to a film when a control surfactant is used.

Stability of a coating or film using the crosslinkable surfactant of the present invention is another beneficial property. The degree of stability of a film can be indicated by the number of double bonds in Tung oil acid derivatives remaining unreacted during storage conditions. Since the double bond in Tung oil acid can be susceptible to polymerization in the presence of air, it is important at the double bonds of the Tung oil acid derivative be reacted.

The migration performance property of the crosslinkable surfactant of the present invention can be less than about 50 in one embodiment, between about 40 and 50 in another embodiment, and between about 45 and 48 in still another embodiment. The migration performance property of the crosslinkable surfactant may be measured by the procedure described in the Emulsion Test Methods used in the Examples.

EXAMPLES

The following Examples and Comparative Examples further illustrate the present invention in more detail but are not to be construed to limit the scope thereof.

In the following Examples and Comparative Examples, various terms and designations were used and are explained as follows:

"TOA" stands for Tung oil acid.

"NMR" stands for nuclear magnetic resonance.

"LC-MS" stands for liquid chromatography-mass spectrometer.

"STOA" stands for sulfate of TOA,

"SSA" stands for sulfate of steric acid.

"CMC" stands for critical micelle concentration.

Example 1—General Procedure for the Synthesis of TOA-10

The product produced in this Example is referred to herein as "TOA-10"; and

TOA-10 was prepared as follows:

Tung oil acid (282.3 g, 1.01 mol) was mixed with potassium hydroxide (KOH)

(50 wt % aqueous solution, 1.82 g) in an ethoxylation reactor. Then, the mixture in the reactor was heated to 60° C. under vacuum to remove water from the mixture. After the water was removed from the reactor contents, the resulting mixture in the reactor was continuously heated at 120° C. Thereafter, ethylene oxide (450 g, 10.2 mol) was stepwise added into the reactor based on pressure control. Once the pressure in the reactor was kept the same as the reactor's initial pressure (for example, usually less than 0.02 MPa), the added EO was considered to be fully consumed and the heating of the reactor was stopped. The following is a representation of a chemical scheme of the reaction described above:

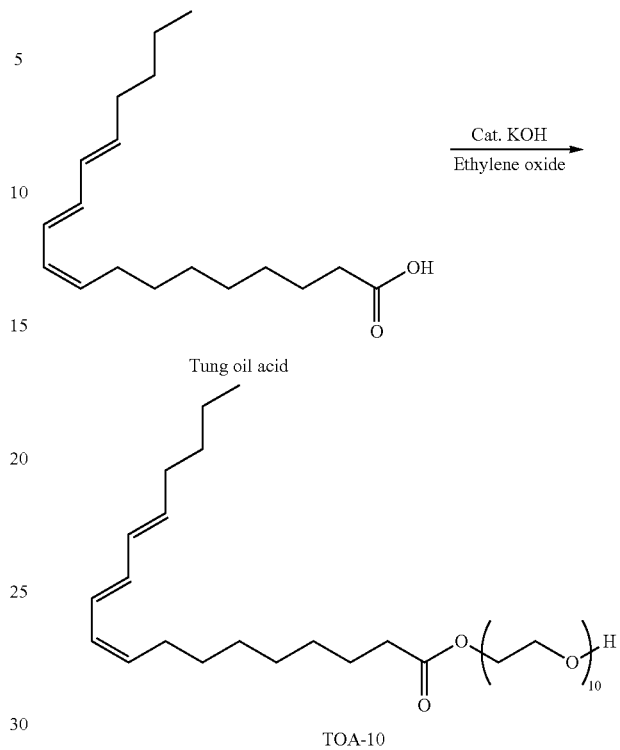

Scheme (I)

Tung oil acid

TOA-10

Characterizing TOA-10

The product TOA-0 produced according to the procedure described above was characterized using measuring techniques and equipment known in the art as follows:

(a) $^1$H NMR Analysis of TOA-10 Mixture

Figure 2:
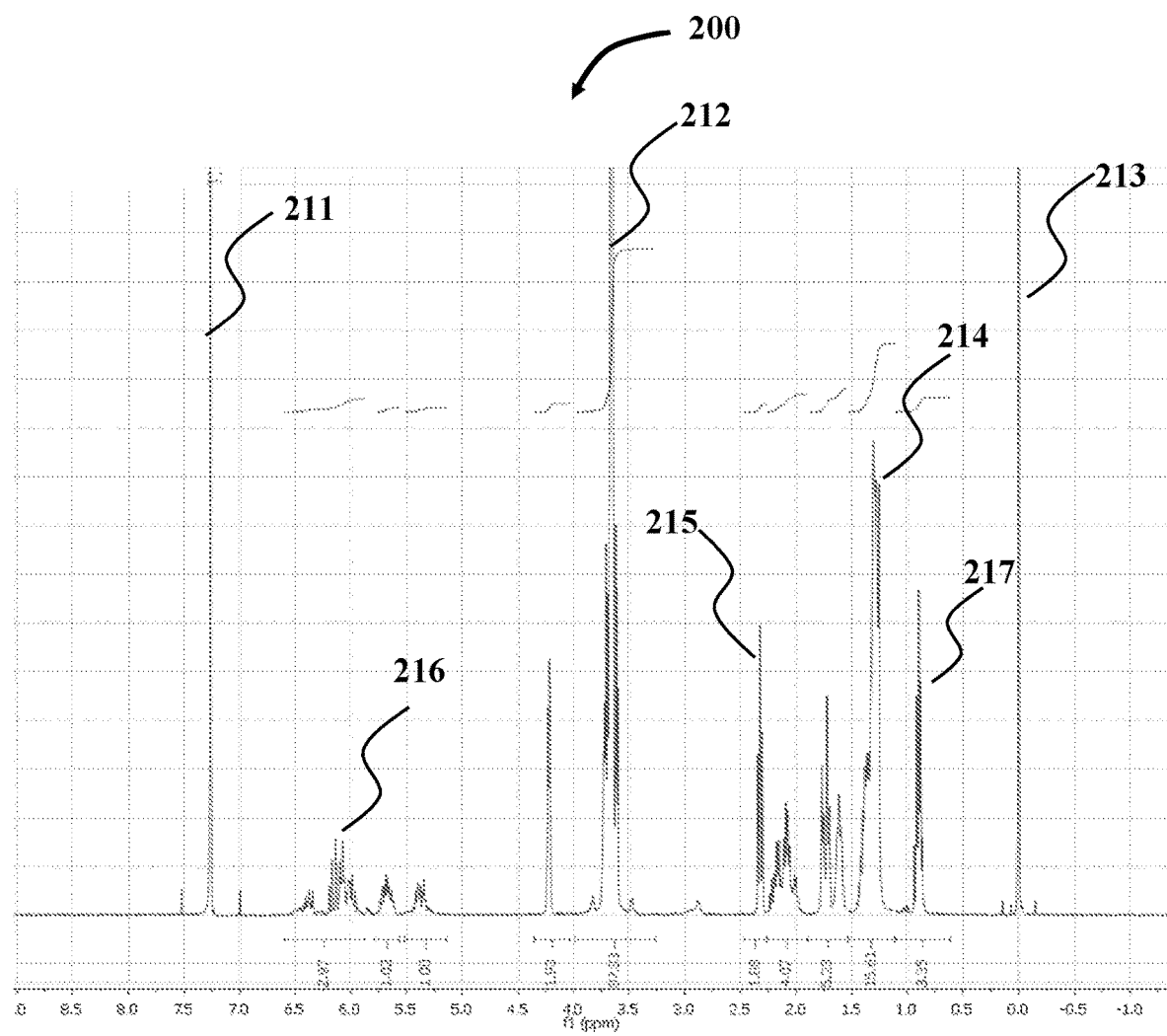
FIG. 2 is a diagram $^1$H NMR spectra of Tung oil acid-10 (TOA-10) showing the chemical structure of TOA-10.

An NMR analysis was carried out in chloroform-d (CDCl$_3$) solvent. The NMR graph for the analysis is shown in FIG. 2. In FIG. 2, the NMR graph shows a series of peaks generally indicated by numeral 200 including, for example, peak 211 which shows CDCl$_3$ solvent residual signal; peak 212 which shows (CH$_2$O)n area signals; peak 213 which shows tetramethylsilane (TMS, internal standard) residual peaks; peaks 214 and 215 which show (CH$_2$) in Tung oil part signals; peak 216 which shows (CH=C—CH=C—CH=C) area signals; and peak 217 which shows CH$_3$ signal.

(b) LC-MS Analysis of Final Product

Tung oil acid is a mixture known to have the components described in Table I.

TABLE I

| Component | Content |
|---|---|
| alpha-eleostearic acid (3 double bonds) | 82.0% |
| linoleic acid (2 double bonds) | 8.5% |
| palmitic acid (1 double bond) | 5.5% |
| oleic acid (saturated fatty acid) | 4.0% |

Figure 3:
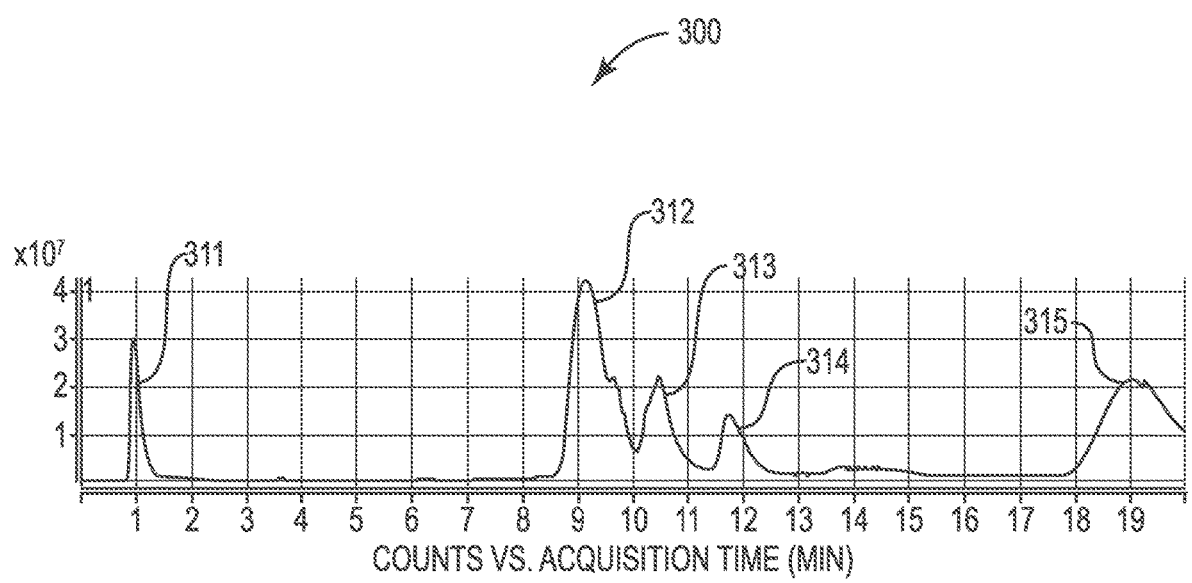
FIG. 3 is a diagram liquid chromatography-mass spectrometer analysis spectra showing the component of TOA-10.

Therefore, in the LC-MS spectra of the final product, the Target, Target+2H, Target+4H, and Target+6H derivatives can be observed. The characterizations set forth in Table II confirm that the mixture structure was that of the desired product TOA-10. FIG. 3 shows the LC-MS spectra of the final TOA-10 product. In FIG. 3, the LC-MS spectra shows a series of peaks generally indicated by numeral 300 including, for example, peaks 311-315; and the corresponding structures of such peaks are described in Table II as follows:

TABLE II

| Peak | Observed Ion | Tentative ID |
|---|---|---|
| 311 | 388.2569-740.4669, spaced by 44, Example: m/z, Ion, Formula, 388.2569, (M + NH4)+, C16 H38 N O9 | H—(OC$_2$H$_4$)$_n$—OH |
| 312 | 604.4468-1000.6838, spaced by 44, Example: m/z, Ion, Formula, 604.4468, (M + NH4)+, C32 H62 N O9 | Target molecules or isomers |
| 312 | 606.462-958.6724, spaced by 44, Example: m/z, Ion, Fonnula, 606.4623, (M + NH4)+, C32 H64 N O9 | Target +2H or isomers |
| 313 | 608.4783-1004.715, spaced by 44, Example: m/z, Ion, Formula, 608.4783, (M + NH4)+, C32 H66 N O9 | Target +4H or isomers |
| 314 | 610.4936-1006.7305, spaced by 44, Example: m/z, Ion, Formula, 610.4936, (M +NH4)+, C32 H68 NO9 | Target +6H or isomers |
| 315 | 864.6618-1216.8719, spaced by 44, Example: m/z,Ion,Forrnula, 864.6618, (M + NH4)+,C50 H90 N O10 | 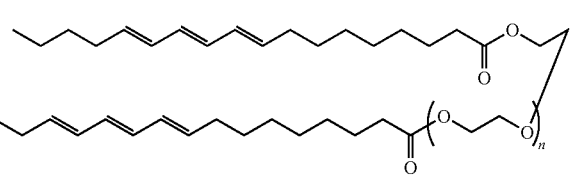 or isomers |

Example 2—General Procedure for the Synthesis of TOA-7

The product produced in this Example is referred to herein as "TOA-7"; and TOA-7 was prepared as follows:

Tung oil acid (306.3 g, 1.10 mol) was mixed with KOH (50 wt % aqueous solution, 1.98 g) in the ethoxylation reactor. Then, the mixture in the reactor was heated to 60° C. under vacuum to remove water. After water removal, the mixture in the reactor was continuously heated to a temperature of 120° C. Afterwards, ethylene oxide (340 g, 7.7 mol) was stepwise added into the reactor based on pressure control. Once the pressure in the reactor was kept same as its initial pressure (usually, less than 0.02 MPa), the EO is considered fully consumed in the reaction and the heating was stopped. The TOA-7 molecule is a mixture with different EO repeat units. The average EO repeat unit was 7. The following is a representation of a chemical scheme of the reaction described above:

Scheme (II)

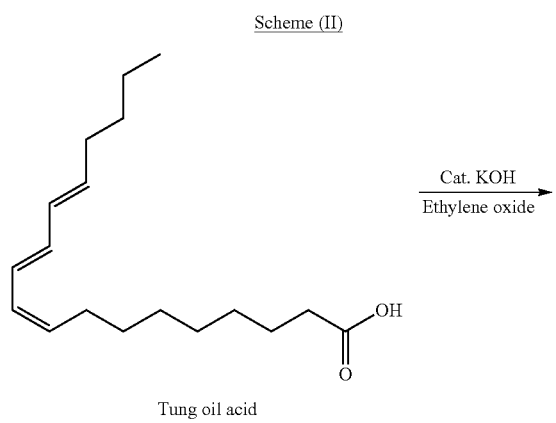

Tung oil acid

-continued

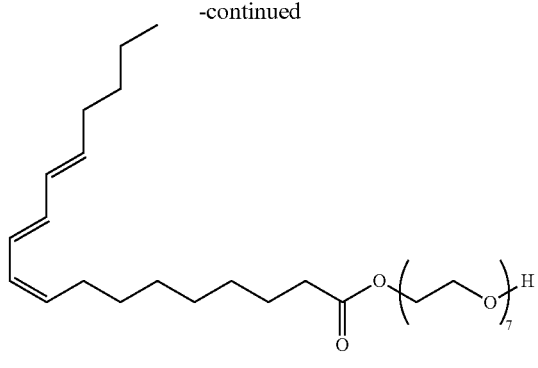

TOA-7

Characterizing TOA-7

Figure 4:
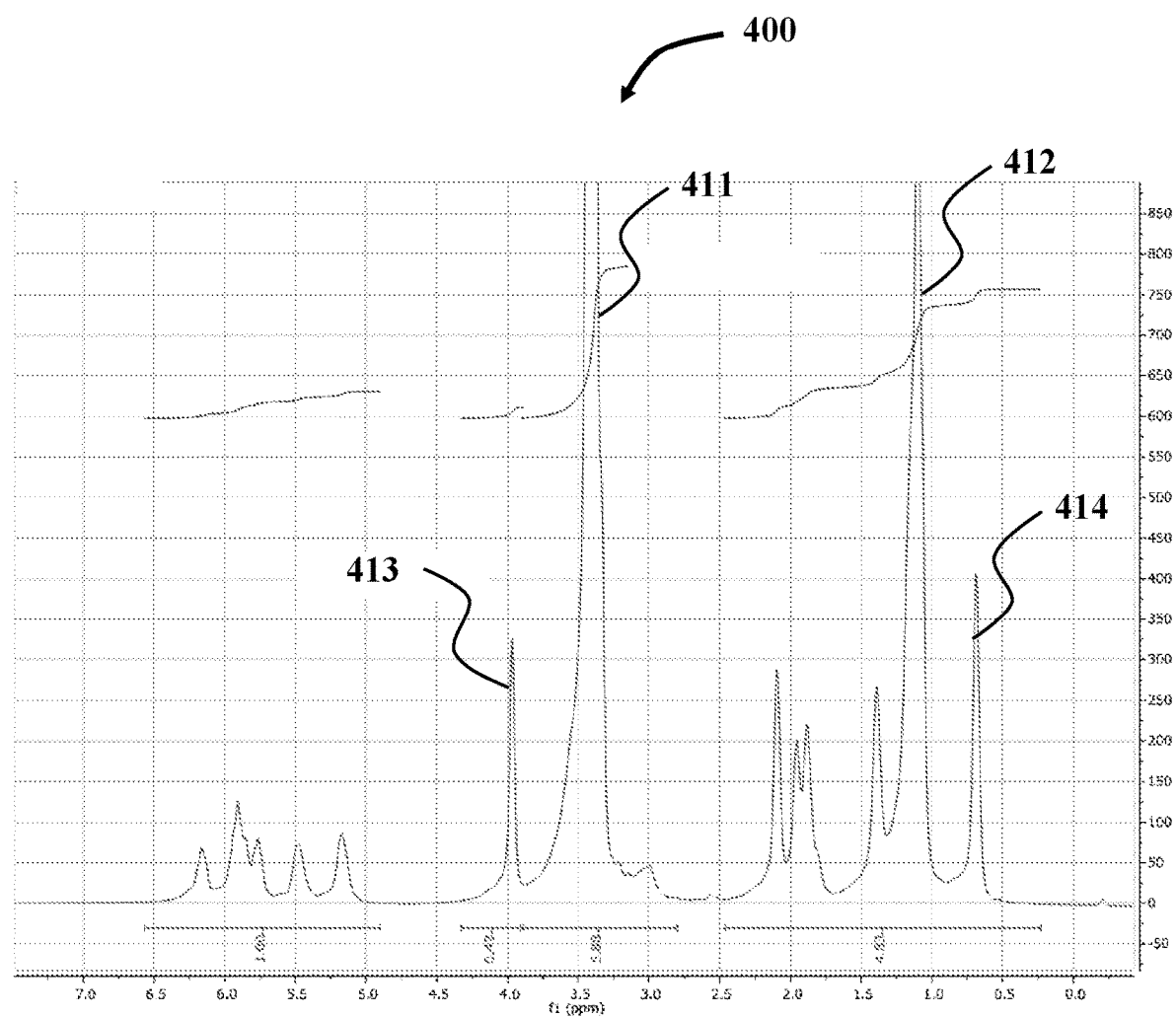
FIG. 4 is a diagram $^1$H NMR spectra of Tung oil acid-7 (TOA-7) showing the chemical structure of TOA-7.

The product TOA-7 produced according to the procedure described above was characterized using conventional measuring techniques and equipment as follows:

(a) $^1$H NMR Analysis of TOA-7 Mixture:

$^1$H NMR analysis was carried out in dichloromethane-d2 (CD$_2$Cl$_2$) solvent and the results are shown in the NMR graph of FIG. 4. In FIG. 4, the NMR graph shows a series of peaks generally indicated by numeral 400 including, for example, peak 411 which shows (CH$_2$O), groups; peak 412 which shows CH$_2$ groups in Tung oil aliphatic parts; peak 413 which shows CH$_2$OH group; and peak 414 which shows CH$_3$ group.

Figure 5:
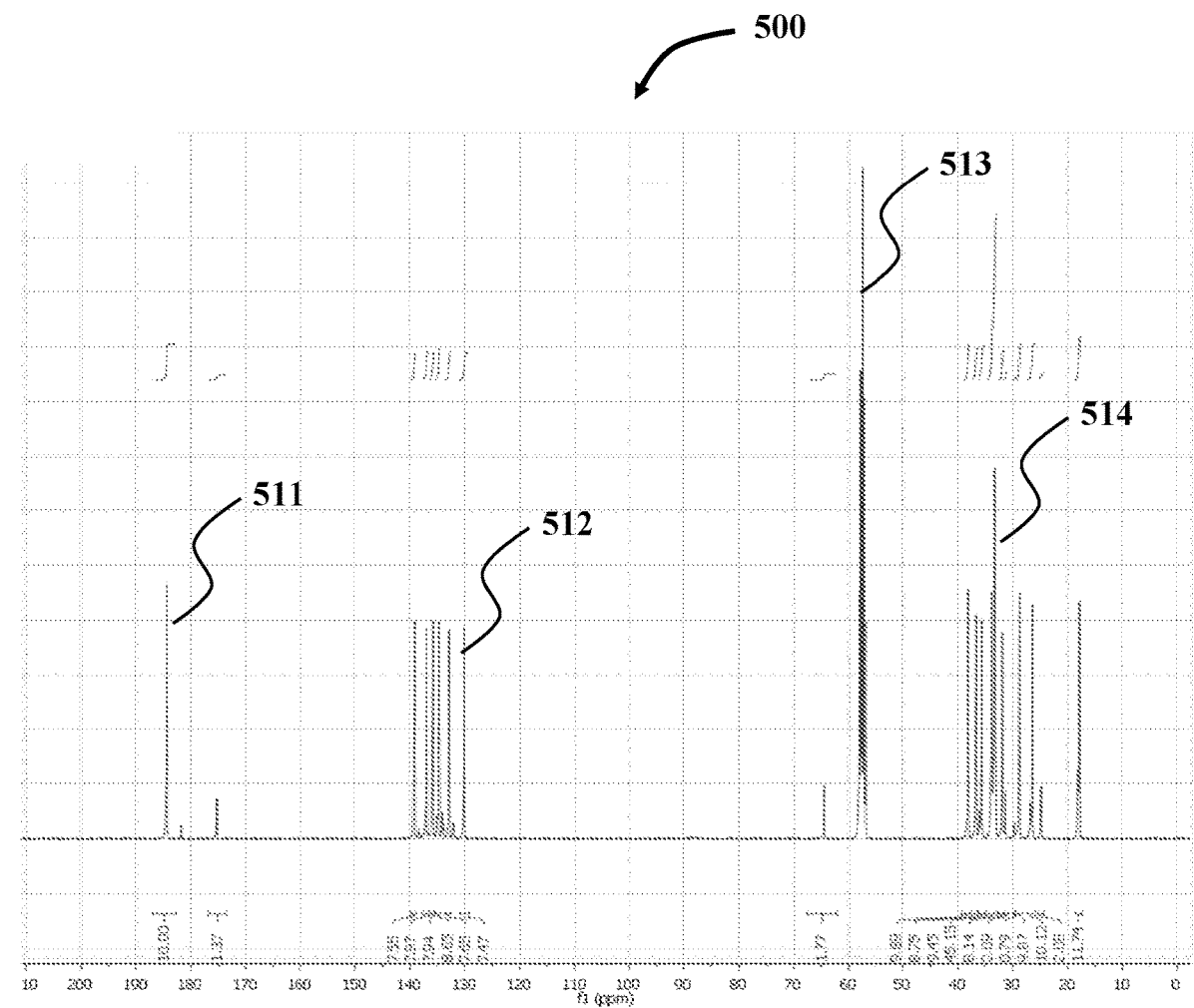
FIG. 5 is a diagram $^{13}$C NMR spectra of TOA-7 showing the chemical structure of TOA-7.

(b) $^{13}$C NMR Analysis (C13ig):

$^{13}$C NMR analysis was carried out in CD$_2$Cl$_2$ and is shown in the NMR graph of FIG. 5. In FIG. 5, the NMR graph shows a series of peaks generally indicated by numeral 500 including, for example, peak 511 which shows C=O group; peak 512 which shows CH=C—CH=C—CH=C area; peak 513 which shows (CH$_2$O)n; and peak 514 which shows aliphatic carbons in Tung oil parts.

Example 3—General Procedure for the Synthesis of STOA-10

The product produced in this Example is referred to herein as "STOA-10"; and STOA-10 was prepared as follows:

To a nitrogen ($N_2$) protected three neck flask was added $NH_2SO_3H$ (4.85 g, 50 mmol) and an inhibitor 2, 6-di-tert-butyl-4-methylphenol (BHT) (40 mg, inhibitor). After that, TOA-10 (36 g, 50 mmol) was loaded. The resulting mixture was allowed to react at 85° C. for three days with mechanical stirring. When the reaction was complete, a high viscosity mixture was formed. Water (133 mL) was added to quench the reaction. STOA-10 aqueous was afforded with 30% solid content. The following is a representation of a chemical scheme of the reaction described above:

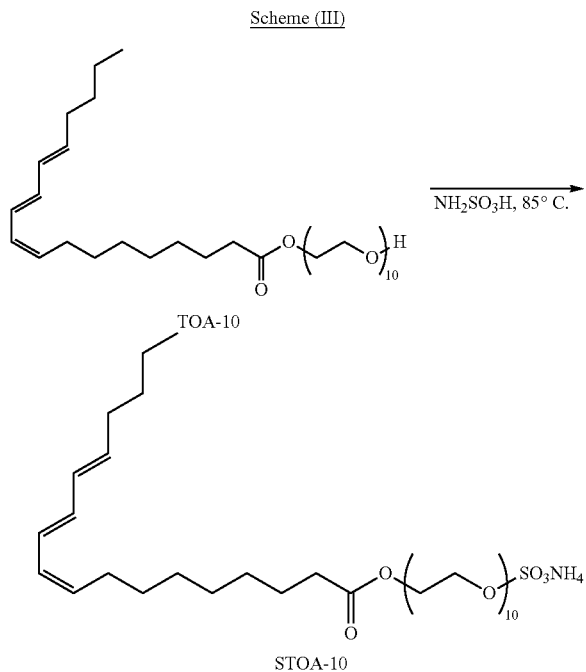

Scheme (III)

Characterizing STOA-10

Figure 6:
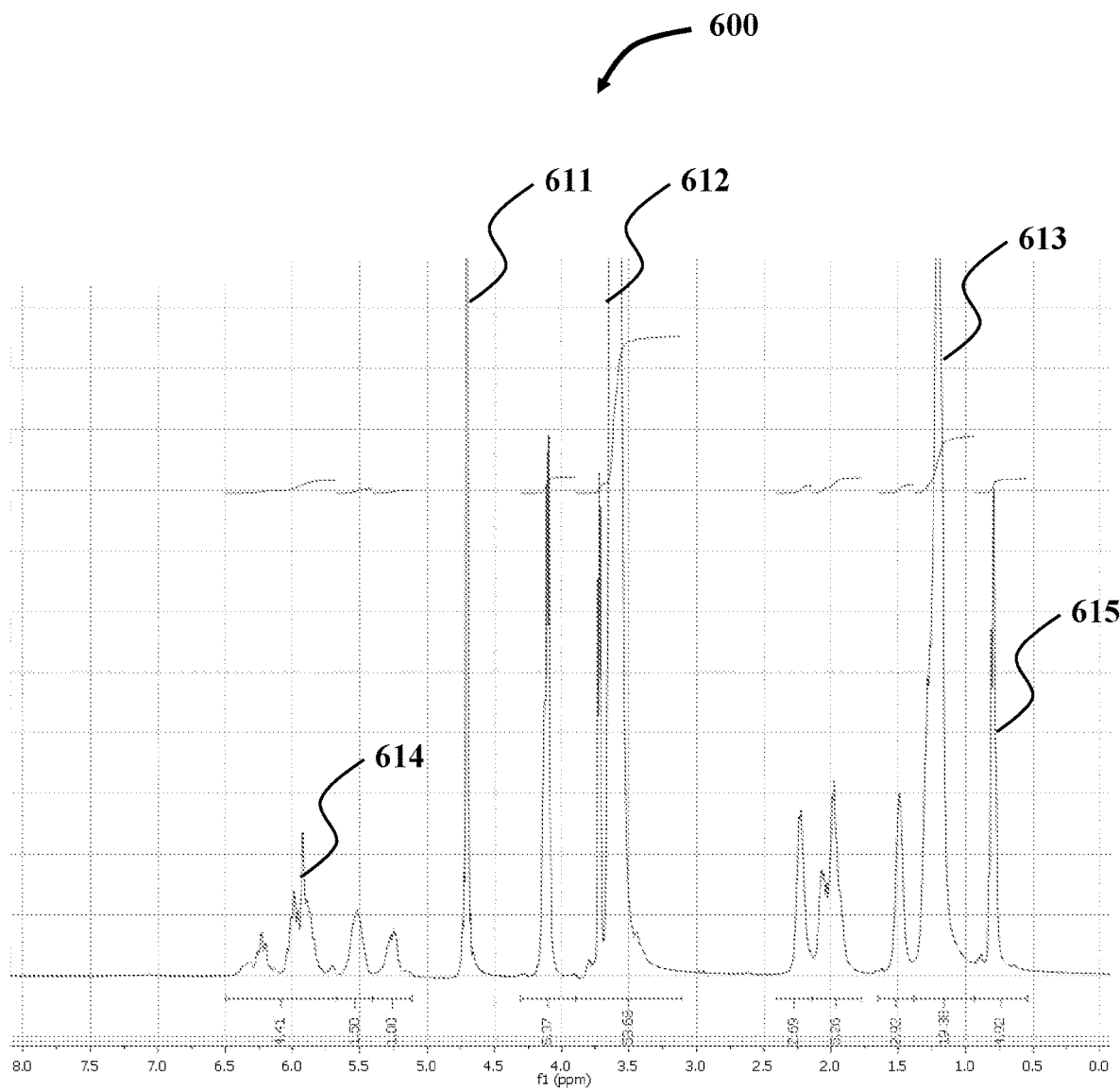
FIG. 6 is a diagram $^1$H NMR spectra of sulfate salt of Tung oil acid-10 (STOA-10) showing the chemical structure of STOA-10.

The STOA-10 prepared above was solved in deuterium oxide ($D_2O$), also known as heavy water) and characterized by $^1H$ NMR analysis and is shown in the NMR graph of FIG. 6. In FIG. 6, the NMR graph shows a series of peaks generally indicated by numeral 600 including, for example, peak 611 which shows $D_2O$ solvent residual; peak 612 which shows $(CH_2O)_nCH_2OSO_3NH_4$; peak 613 which shows $CH_2$ groups in Tung oil part; peak 614 which shows CH=C—CH=C—CH=C area; and peak 615 which shows $CH_3$ group.

Example 4—General Procedure for the Synthesis of STOA-7

The product produced in this Example is referred to herein as "STOA-7"; and
STOA-7 was prepared as follows:

To a $N_2$ protected three neck flask was added $NH_2SO_3H$ (6.8 g, 70 mmol), urea (4.2 g, 70 mmol) and BHT (50 mg, inhibitor). After that, TOA-7 (41.02 g, 70 mmol) was loaded. The resulting mixture was allowed to react at 85° C. overnight with mechanical stirring. When the reaction was complete, a high viscosity mixture was formed. Water (159 mL) was added to quench the reaction. STOA-7 aqueous was afforded with 30% solid content. The following is the chemical reaction scheme of the above reaction:

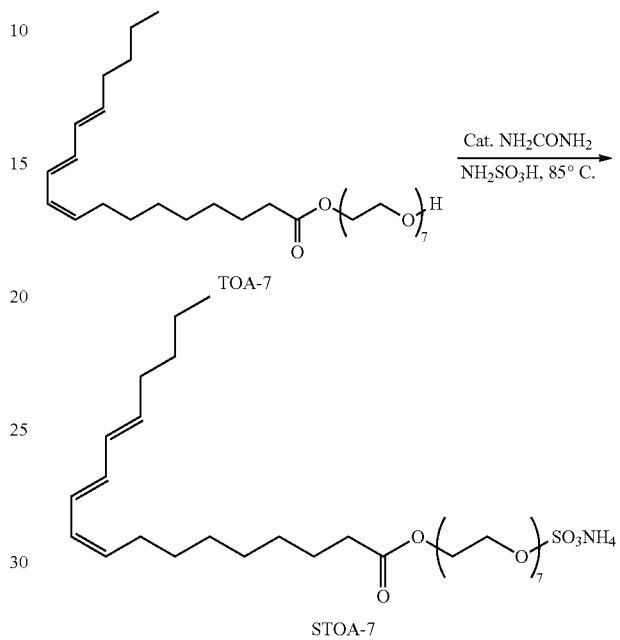

Scheme (IV)

Characterizing STOA-7

Figure 7:
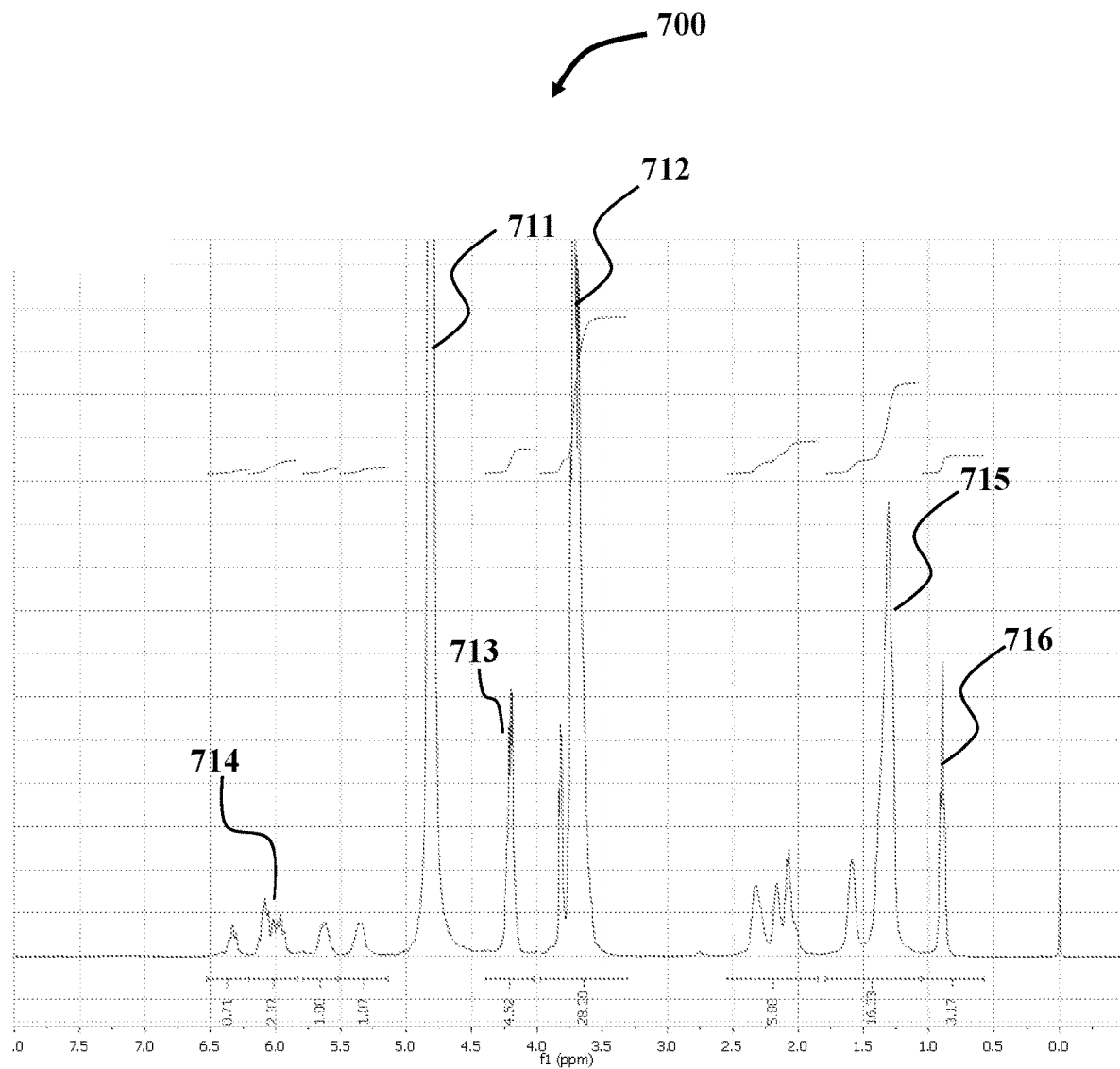
FIG. 7 is a diagram $^1$H NMR spectra of sulfate salt of Tung oil acid-7 (STOA-7) showing the chemical structure of STOA-7.

STOA-7 was solved in $D_2O$ and characterized by $^1H$ NMR analysis. The NMR graph for the $^1H$ NMR analysis is shown in FIG. 7. In FIG. 7, the NMR graph shows a series of peaks generally indicated by numeral 700 including, for example, peak 711 which shows $D_2O$ solvent residual; peak 712 which shows $(CH_2O)_n$; peak 713 which shows $CH_2OSO_3NH_4$ peak, peak 714 which shows CH—C—CH=C—CH=C area; and peak 715 which shows $CH_3$ group.

Comparative Example A—General Procedure for the Synthesis of SSA-10 (Control Surfactant)

The product produced in this Example is referred to herein as "SSA-10"; and to learn the reactivity of C=C bonds in Tung oil derivatives, and to minimize experimental error, one control surfactant was prepared with saturated C18 fatty acid (stearic acid) following the following process:

Fatty acid (stearic acid, 493.8 g) was mixed with KOH (50 wt % aqueous solution, 1.94 g) in an alkoxylation reactor. Then, the mixture in the reactor was heated to 60° C. under vacuum to remove water from the mixture. After the water was removed from the reactor contents, the resulting mixture in the reactor was continuously heated at 120° C. Thereafter, ethylene oxide (10 mol) was stepwise added into the reactor based on pressure control. Once the pressure in the reactor was maintained at the same pressure as the reactor's initial pressure (for example, usually less than 0.02 MPa), the added EO was considered to be fully consumed and the heating of the reactor was stopped. The following is a representation of a chemical scheme of the reaction described above:

The following is the chemical reaction scheme of the above reaction:

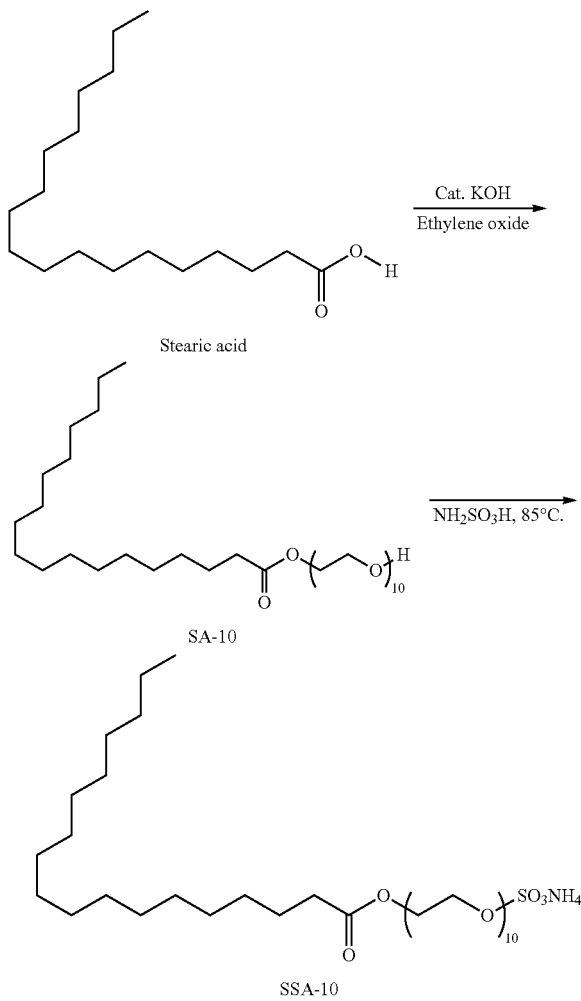

Scheme (V)

Basic Characterization of Surfactant Properties

TABLE III

Surfactant Properties

| | Example 1 | Example 2 | Comparative Example A |
|---|---|---|---|
| Property | STOA-7 | STOA-10 | SSA-10 |
| Active content (wt %) | 30 | 30 | 30 |
| Appearance (20° C.) | yellow viscous liquid, opaque | orange viscous liquid, opaque | white paste |
| Surface tension at CMC (mN/m, 20° C.) | 37.6 | 39.9 | 40.3 |
| CMC (ppm) | 375 | 450 | 650 |
| Foam height (Ross Miles, 0/ 5 min at 0.2 wt %) | 125/95 | 115/80 | 32/20 |
| $Ca^{2+}$ stability (%, $CaCl_2$, 1 wt %) | 35 | >40 | >40 |

From the results in Table III, it was observed that both STOA-7 (Example 1) and STOA-10 (Example 2) were opaque liquid with 30% solid content. However, SSA-10 (Comparative Example A) with the same solid content showed very poor flowability. It is theorized that the poor flowability for SSA-10 is due to less steric hindrance and good packing of saturated C18 chains. In addition, the results in Table III show that the surface tension is relatively high for the three samples. And, the CMC for the three samples is in an appropriate range to use in emulsion polymerization.

Examples 6 and 7 and Comparative Example C—Application of STOA-7 and STOA-10 in Emulsion Polymerization The basic formulation 1 of styrene-butyl acrylate emulsion includes the following monomers: butyl acrylate, styrene, acrylamide and acrylic acid; an initiator such as ammonium persulfate; and an anionic surfactant at 0.834 per hundred grams of monomer (phm). STOA-7, STOA-10 or SSA-10 is used as the anionic surfactant in emulsion polymerization. The glass transition temperature (Tg) of the resulting emulsion is about 22° C.

General Polymerization Procedure of Styrene-Butyl Acrylate Emulsion

Step (1): prepare monomer emulsion with a first portion (0.580 phm) of the anionic surfactant, sodium bicarbonate, water and the above mentioned monomers;

Step (2): add a second portion (0.254 phm) of the anionic surfactant and water into the reactor, start heating the reactor to a temperature of about 85° C.; then add the first portion of ammonium persulfate (1.2 g) to the reactor, Step (3): start dropwise addition of the pre-emulsion with the aqueous solution of the second portion of ammonium persulfate (1.8 g in 88 g water) during 3 hr;

Step (4): after the dropwise addition, keep the emulsions aging at 85° C. for 1 hr;

Step (5): once cooling down to 65° C., re-dox initiator was added to further consume the residual monomers for 30 min; and Step (6): cool down to 40° C., and adjust pH to a pH of 7-8 by using aqueous ammonia; the polymer emulsion is obtained after filtration.

Emulsion Test Methods

Polymerization Residue

Filter the resulting emulsion, collect reaction aggregates in the filter, rinse the filter by tap water, dry it at ambient temperature and weigh the collected aggregates to determine the amount of polymerization residue. A ratio of the weight of aggregates to the total weight of the emulsion by unit of g/kg is used to express the polymerization stability. The lower the value, the better the polymerization stability is.

Particle Size and Distribution Measurements

By using a Zeta Potential particle size analyzer (an instrument for characterizing nano- and microparticles in dispersions and solutions) (manufactured by Malvern) an average particle diameter and distribution of the emulsion was measured.

$Ca^{2+}$ Stability Test $CaCl_2$ aqueous solution (concentration at 10 wt %) was added into 20 mL of emulsion; after manual mixing, the $CaCl_2$-containing emulsion was kept at room temperature for 48 hr. Any appearance of agglomeration or non-homogeneity in the emulsion indicates failure in the $Ca^{2+}$ stability test.

Foam Height Measurement

Weigh 200 g of emulsion in a plastic beaker, measure the height of emulsion surface to the edge of the beaker, and measure again the height of the liquid surface to the edge of the beaker after high speed dispersion (4,000 rpm) for 30 min; the height change essentially results from the foam formed during the presence of shearing effect.

Mechanic Stability Test

Weigh 400 g of emulsion in a plastic beaker, after high speed dispersion (4,000 rpm) for 30 min, filter the emulsion; collect all aggregates in the filter, and after drying the aggregates at ambient temperature, weigh the dried aggregates. The lower the weight value of the aggregates, the better the mechanic stability is of the emulsion.

Water Whitening Resistance Test

Add 4 wt % of coalescent in the emulsion; after manual mixing, emulsion film was spread on glass plate surface with the thickness around 100 micrometers (μm). The film was dried in air at ambient temperature for 24 hr, the glass plate with emulsion film was then immersed in tap water. The appearance of the film was checked after 24 hr as a measure of the water whitening resistance of these emulsion films. The water penetration between the emulsion film and the substrate results in the visual observation of whitening; as a result, less whitening indicates good water whitening resistance.

Comparison of Emulsion Properties

Following the above mentioned process, three emulsions were prepared with three surfactants, respectively. The only difference in these three emulsions is the use of the different anionic surfactants in the emulsions.

TABLE IV

General Emulsion Properties

|  | Example 6 | Example 7 | Comparative Example C |
|---|---|---|---|
| Anionic surfactant | STOA-7 | STOA-10 | SSA-10 |
| Solid content (wt %) | 46.3 | 46.6 | 46.6 |
| Polymerization residue (g/kg of emulsion) | 0.59 | 0.95 | 2.53 |
| Particle size (nm) | 134.9 | 134.3 | 164.4 |
| Peak width (nm) | 35.3 | 31.0 | 41.2 |
| pH | 6.1 | 5.9 | 6.4 |
| Viscosity (cP, #63 spindle, 100 rpm, 25° C.) | 649 | 773 | 887 |
| $Ca^{2+}$ stability (10% $CaCl_2$, aq.) | 11% | 14% | 12% |
| Foam height (mm) | 23 | 36 | 12 |
| Mechanical stability (g/kg of emulsion) | 0.01 | 0.02 | 0.02 |

As described in Table IV, the results show that the emulsions with both Examples 6 and 7 had a relatively low polymerization residue, which indicates better polymerization stability. In addition, the particle size of the two emulsions of Examples 6 and 7 are much smaller than the emulsion with SSA-10 (Comparative Example C). In fact, due to the insufficient emulsification power of SSA-10, the pre-emulsion of SSA-10 is not stable, which impacted the particles stability during the polymerization process.

In terms of emulsion $Ca^{2+}$ stability, the performance of Examples 6 and 7 is good in accordance with the $Ca^{2+}$ stability of each surfactant itself.

Surprisingly, the three emulsions (Examples 6 and 7, and Comparative Example C) had a low foaming height after being processed through a high speed dispersion even though STOA-7 and STOA-10 are not really low foam surfactants.

Examples 8 and 9 and Comparative Examples D and E

Comparison of Emulsions Water Resistance

Water resistance is a very important criterion in customers' emulsion evaluation. In fact, many customers use reactive surfactants essentially for water resistance improvement. In lab work, water whitening resistance is used to as a simplified test to indicate water resistance performance. The water penetration between the emulsion film and the substrate results in the visual observation of whitening; as a result, less whitening signifies good water whitening resistance.

In this test, to amplify the effect of surfactants on water whitening resistance and its crosslinking efficiency, 1.2 phm of surfactant was intentionally post-added into the prepared emulsions. Therefore, the final amount of surfactants in the emulsion was around 2.0 phm based on monomer weight.

Two groups of water whitening resistance tests were run. In Group I, only 4% wt. of coalescent was mixed with the emulsion; in Group II, same level of coalescent as well as 60 ppm of cerium 2-ethyl hexanoate, $Ce(2-EHA)_2$ (Redox catalyst), were introduced into the emulsions.

The color measurement system used in the Examples is based on a "Lab" color model known to those skilled in the art. The terminology "Lab" originates from the three dimensions of the Hunter 1948 color space, which are "L", "a", and "b". In these Examples, "L" means lightness or luminosity according to a rating scale of from "0 to 100"; wherein "0" means black and "100" means white; "a" means from green to magenta and "b" means from blue to yellow. Since work is done on black plate, the data "L" is more important to show the whitening effect using the process of the present invention.

TABLE V

Water Whitening Resistance Test Results

| Example | Surfactant Used | Group I | | | | Group II | | | |
|---|---|---|---|---|---|---|---|---|---|
|  |  | L | a | b | ΔL | L | a | b | ΔL |
| Comparative Example D (blank plate with no film) | Ref[1] | 25.00[2] | −0.25 | −0.70 | — | 25.00 | −0.25 | −0.70 | — |
| Example 8 | STOA-7 | 47.72 | −1.75 | −19.96 | 22.72 | 43.35 | −0.78 | −19.31 | 18.35 |
| Example 9 | STOA-10 | 46.83 | −1.32 | −20.02 | 21.83 | 43.36 | −0.97 | −21.30 | 18.36 |
| Comparative Example E (conventional) | SSA-10 | 50.95 | −1.16 | −18.29 | 25.95 | 49.73 | −0.62 | −18.54 | 24.73 |

Notes for Table V:
[1]"Ref" means the measurement was done with the black plate itself without coating film; as a result, same data in both groups.
[2]Data shown in Table V are the average of three measurements.

It is clearly shown, from the data in Table V, that both crosslinkable surfactants of Examples 8 and 9 are slightly more advantageous on L in Group I; while Examples 8 and 9 shows a net reduction of L in Group II, which means each surfactant exhibited a less whitening effect. As some crosslinkable surfactant is post-added in the emulsion, this could be understood that after 24 hr drying in atmosphere, the additional surfactant was not fully crosslinked in Group I; but in Group II, in the presence of only 60 ppm of redox catalyst, the crosslinking process was accelerated, which resulted in the netter reduction of L in Group II.

In summary, the present invention provides a new type of crosslinkable surfactant with a Tung oil acid derivative structure (e.g., STOA surfactants). The crosslinking of Tung oil acid derivative structure can occur during a polymerization process, during a film-forming process; or during both a polymerization and film-forming process. Compared to a non-crosslinkable surfactant (e.g., SSA surfactants) as a control, the STOA surfactants, for example, can advantageously increase the water whitening resistance property of films produced by emulsion polymerization using the STOA surfactants. The crosslinking step may be accelerated with the addition of a redox catalyst to the emulsion process.

What is claimed is:

1. A monomer emulsion composition comprising a pre-emulsion of: a crosslinkable surfactant comprising a reaction product of (a) Tung oil acid and (b) at least one alkylene oxide forming a Tung oil derivative, wherein the Tung oil derivative has the following chemical Structure (II):

Structure (II)

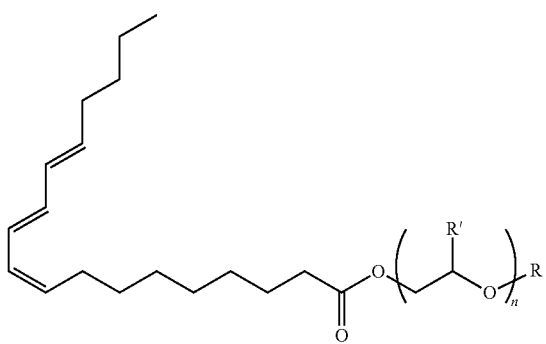

wherein R is hydrogen, $SO_3^-$ or $PO_3^-$, R' is hydrogen or C1-C6 alkyl group, and n is a number value of from 1 to 15; or

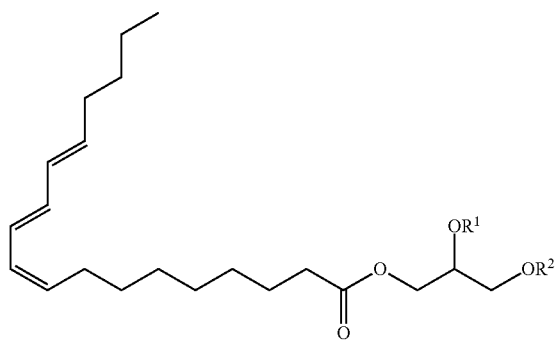

wherein $R^1$ and $R^2$, each individually, is an alkyl having from C1 to about C10 carbon atoms, an aryl having from C5 to about C10 carbon atoms, a polyol, a polyol ester, hydrogen, $SO_3^-$, or $PO_3^-$, and wherein $R^1$ and $R^2$ can be the same or different;

at least one monomer; and water.

2. The monomer emulsion composition of claim 1, wherein the alkylene oxide is selected from the group consisting of ethylene oxide, propylene oxide, butylene oxide, and mixtures thereof.

3. The monomer emulsion composition of claim 1, wherein the Tung oil derivative has a combined crosslinkable functionality and hydrophobic chain as a Tung oil structure.

4. The monomer emulsion composition of claim 1, wherein the Tung oil derivative has a hydrophilic chain with a polyalkylene oxide glycol derivative or a polyglycerin derivative.

5. The monomer emulsion composition of claim 1, wherein the Tung oil derivative is an ionic form.

6. The monomer emulsion composition of claim 1, wherein the at least one monomer is selected from the group consisting of styrene, butyl acrylate, and mixtures thereof.

7. The emulsion polymerization composition of claim 1 further comprising at least one initiator.

8. The emulsion polymerization composition of claim 7, wherein the at least one initiator is selected from group consisting of potassium persulfate, ammonium persulfate, benzoyl peroxide; and mixtures thereof.

9. A polymerization reaction product made from the emulsion polymerization composition of claim 7.

10. The polymerization reaction product of claim 9, wherein the reaction product is a film or a coating.

11. The film or coating of claim 10, wherein the film or coating exhibits a water whitening resistance property having a luminosity value L from about 45 to about 48.

12. A process for preparing a crosslinkable surfactant comprising reacting (a) Tung oil acid and (b) at least one alkylene oxide forming a Tung oil derivative, wherein the Tung oil derivative has the following chemical Structure (II):

Structure (II)

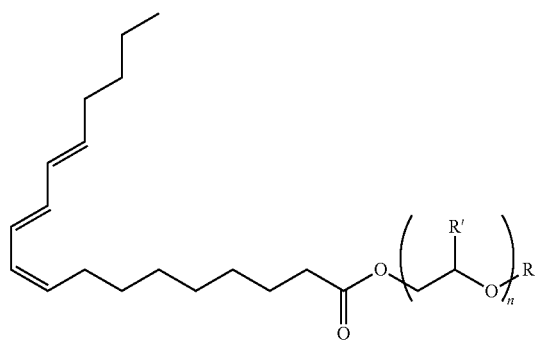

wherein R is hydrogen, $SO_3^-$, or $PO_3^-$ R' is hydrogen or C1-C6 alkyl group, and n is a number value of from 1 to 15; or Structure (III)

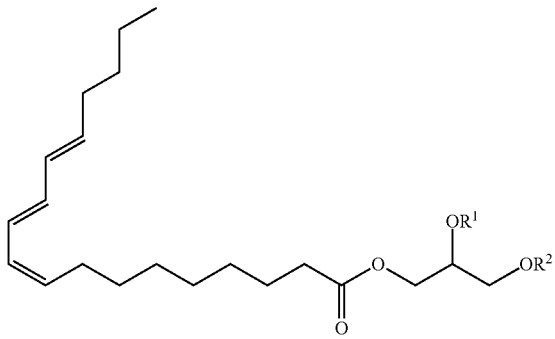

wherein R¹ and R², each individually, is an alkyl having from C1 to about C10 carbon atoms, an aryl having from C5 to about C10 carbon atoms, a polyol, a polyol ester, hydrogen, $SO_3^-$, or $PO_3^-$; and wherein R¹ and R² can be the same or different.

13. A process for preparing a monomer emulsion composition comprising admixing (a) the crosslinkable surfactant comprising the Tung oil derivative of claim 1; (b) at least one monomer; and (c) water.

14. A process for preparing an emulsion polymerization composition comprising admixing (a) the pre-emulsion of claim 1; and (b) at least one initiator.

15. A process for preparing a polymerization reaction product comprising reacting the emulsion polymerization composition of claim 14.

16. The monomer emulsion composition of claim 1, wherein the Tung oil derivative is a non-ionic form.

* * * * *